United States Patent [19]

Pederson et al.

[11] Patent Number: 5,061,018

[45] Date of Patent: Oct. 29, 1991

[54] MICROSCOPE ACCESSORY EQUIPMENT CONTAINER

[75] Inventors: Jane M. Pederson; William R. Johnson, both of Largo, Fla.

[73] Assignee: Time Surgical, Inc., Largo, Fla.

[21] Appl. No.: 590,658

[22] Filed: Sep. 28, 1990

Related U.S. Application Data

[63] Continuation-in-part of Ser. No. 503,271, Apr. 2, 1990, abandoned.

[51] Int. Cl.⁵ ............................................. A47B 81/00
[52] U.S. Cl. .................................... 312/209; 312/328
[58] Field of Search .............. 312/247, 209, 312, 328; 211/133, 13, 163, 205, 84

[56] References Cited

U.S. PATENT DOCUMENTS

| | | | |
|---|---|---|---|
| 1,861,802 | 6/1932 | Kelly | 312/328 X |
| 4,572,594 | 2/1986 | Schwartz | 312/209 |
| 4,573,948 | 3/1986 | Biraghi et al. | 312/247 X |
| 4,607,897 | 8/1986 | Schwartz | 312/209 |
| 4,953,601 | 9/1990 | Herdies | 312/247 X |

Primary Examiner—Joseph Falk
Attorney, Agent, or Firm—Herbert W. Larson

[57] ABSTRACT

The microscope accessory equipment container is mounted on a surgical stand having an upright post mounted on a supporting member with one or more microscopes and supporting apparatus pivotably mounted on an upper portion of the post. One or more microscope accessory equipment containers are mounted below the microscopes. Each container has a ceiling two side walls, a front and rear wall and a floor. A hinged lid on a front edge of the ceiling descends downwardly to rest on a top edge of the front wall to form an enclosure for storing microscope accessories.

20 Claims, 5 Drawing Sheets

MICROSCOPE ACCESSORY EQUIPMENT CONTAINER

PRIOR APPLICATION

This application is a continuation-in-part of application Ser. No. 07/503,271, filed Apr. 2, 1990, now abandoned.

BACKGROUND OF THE INVENTION

1. Field of The Invention

This invention relates generally to surgical operating room furniture, and, more specifically, to a microscope accessory equipment container designed to store, protect, and make readily available a substantial number of different types of surgical microscope accessories and other equipment for supporting microsurgery.

2. Description of The Prior Art

Since the surgical microscope was introduced, circa 1960, numerous accessories have been developed, thus allowing a single microscope to be used by various surgical specialties such as ophthalmology, neurosurgery, hand surgery and otolaryngology. Surgical microscopes attached to a floor stand are intended to offer portability, and are designed to be utilized by various surgical specialties. They are easily and frequently moved from one hospital operating room to another. Each surgical specialty usually requires a different configuration of the surgical microscope. Within each specialty there also exist individual surgeons' preferences for accessory equipment which dictate yet additional configurations of the microscope. Heretofore, these accessories have been stored in a rather haphazard fashion, often in a location distant from the microscope and without regard to the safe keeping of expensive precision accessories which often contain critical optical components. It is not unusual for the owners of surgical microscopes to incur significant replacement and/or service costs due to improper storage or handling of accessories and associated equipment. A major consideration of this invention is to provide a container for the safe, clean storage of microscope accessories. Additionally, a substantial amount of time is required to reconfigure the microscope each time it is used for a different surgical procedure when accessory equipment is stored in a remote location. This invention reduces the time required to reconfigure a microscope.

One object of the invention is to provide immediate accessibility to accessories with the attachment of the storage container directly to the microscope stand.

An important aspect to consider regarding the invention is the limited availability of space within the operating room. Due to various requirements in patient, surgeon, and equipment positioning around the microscope, it is critical that any attachments to the microscope not obstruct access to the patient or other operating room equipment. Thus, another object of the invention is to provide a mechanism for repositioning the microscope accessory equipment container to accommodate space restrictions. The repositioning mechanism varies slightly depending upon the particular design of the microscope support stand. Approximately seven different configurations of microscope floor stands exist today. A unique aspect of the invention is that it is able to attach to each of the different microscope designs and, with the appropriate mounting mechanism still fulfill its objectives.

SUMMARY OF THE INVENTION

Very generally, the present invention includes a microscope accessory equipment container, suitable for use in the operating room mounted on a microscope post. The container provides for the clean, safe storage of microscope accessories and other microsurgical equipment and supplies. Another aspect of the invention is the mounting mechanism allowing the microscope accessory equipment container to be mounted directly to the microscope stand providing immediate access to stored accessories. A further aspect of the invention is a repositioning mechanism allowing the microscope accessory equipment container to be repositioned as necessary in the operative and storage modalities.

Our storage container has a ceiling with a hinged lid descending from a front edge of the ceiling to rest on a top edge of a front wall. The front wall is joined on opposite side edges to front edges of right and left side walls. The side walls are joined to a floor. Opposite rear side edges of the side walls are joined to an upright back wall. The back wall is joined to a rear edge of the ceiling. The hinged lid spans the gap between the side walls to form a closed container when the hinged lid is resting on the top edge of the front wall.

Up to three containers can be mounted vertically on the microscope post using a back plate to both position the containers and connect with a clamping or other mounting means to the post.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE DRAWINGS

Figure 1:
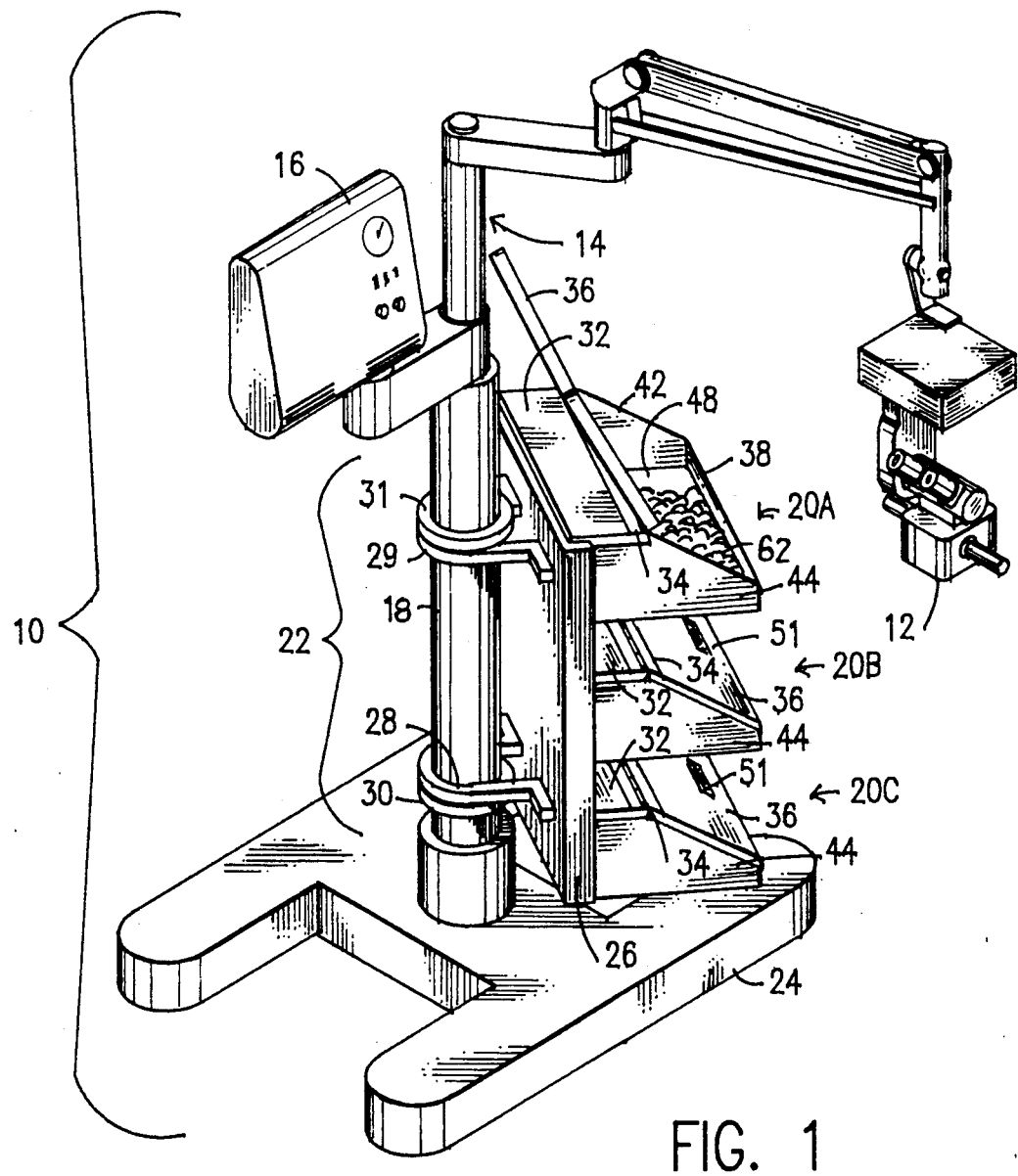
FIG. 1 is a perspective view of the storage containers mounted on a round microscope support stand.

Throughout the following detailed description, the same reference numerals refer to the same elements in all figures.

Figure 2:
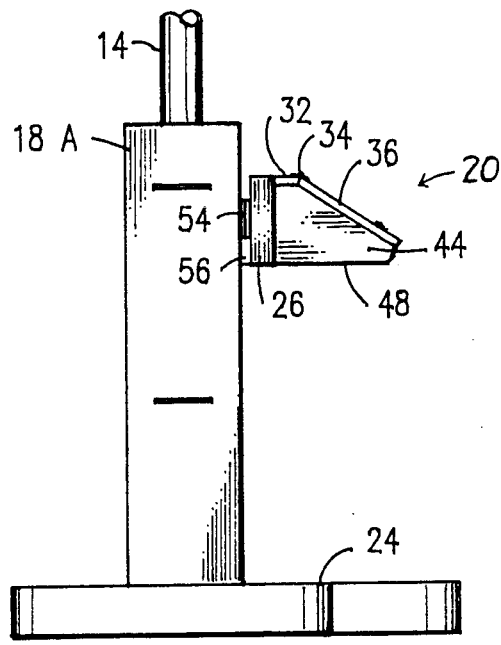
FIG. 2 is a side elevational view of a bottom portion of a four-sided operating microscope support post with a single mounted storage container.

Referring to FIG. 1, the microscope stand 10 has a microscope 12 pivotably mounted on a post 14. A control panel 16 is also pivotably mounted on the post. The microscope 12, and the control panel 16 are mounted on the upper portion of post 14. Three microscope accessory equipment containers 20A, 20B and 20C are pivotably mounted on a lower portion 22 of post 14. Usually the lower portion of post 14 has a larger diameter 18. The post 14 is supported by a base element 24. The post portion 18 can be round as seen in FIG. 1 or squared 18A as seen in FIG. 2.

Figure 7:
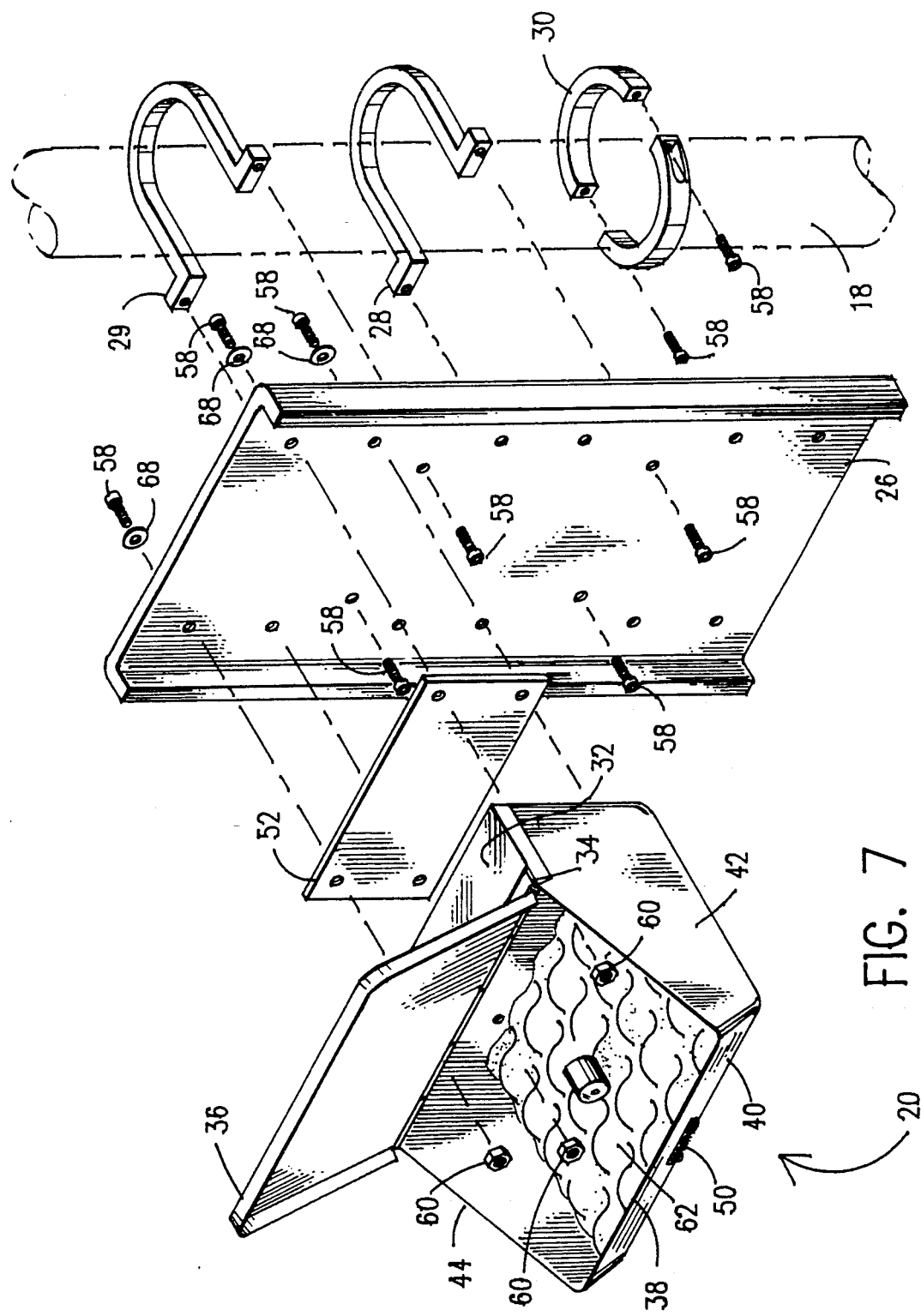
FIG. 7 is an exploded view of a clamp, back plate and container mountable to a round post shown in phantom.
Figure 8:
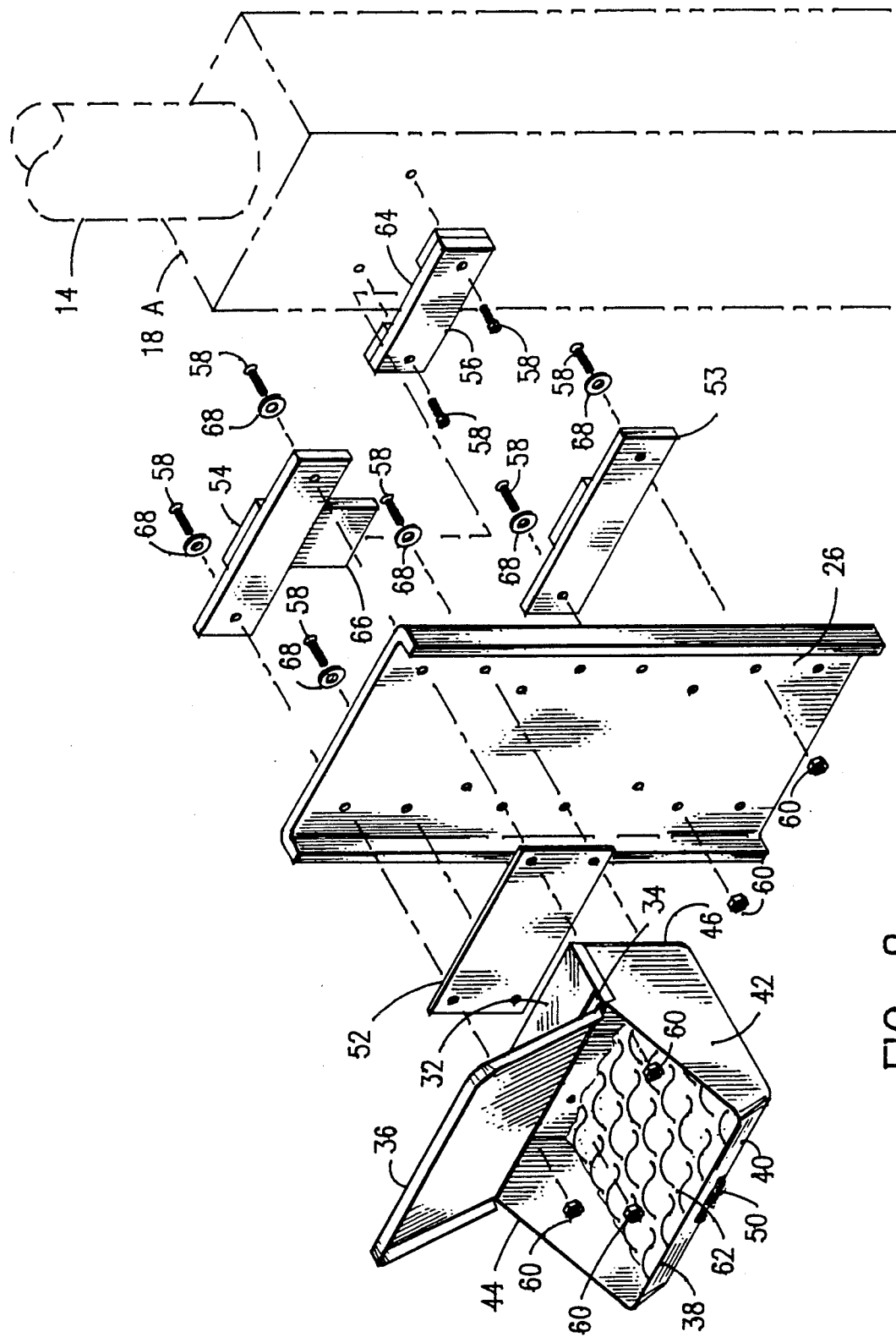
FIG. 8 is an exploded view of the mounting bracket, squared back plate and container mountable to a squared post shown in phantom.

The containers 20A, B and C are bolted to a back plate 26, which is in turn clamped by clamps 28 and 29 to post portion 18 as seen in FIG. 7 or mounted by brackets 54 and 56 to post 18A as seen in FIG. 8.

Each container 20 as seen in FIG. 7 has a top planar surface 32 which has a hinge 34 attached to a front edge. The hinge is connected to a lid or cover 36 which descends downwardly to rest on a top surface 38 of a front wall 40. Right side wall 42 and left side wall 44 join the front wall 40 to the upright back wall 46. A strip of hook or loop material 51 is attached to a front surface of the lid 36 and a complimentary hook or loop material 50 is attached to the front lower edge of wall 40. In a stacked arrangement as shown in FIG. 3, a lifting of lid 36 engages the loop material 51 with the complimentary hook or loop 50 to keep the lid 36 in a raised configuration.

Figure 5:
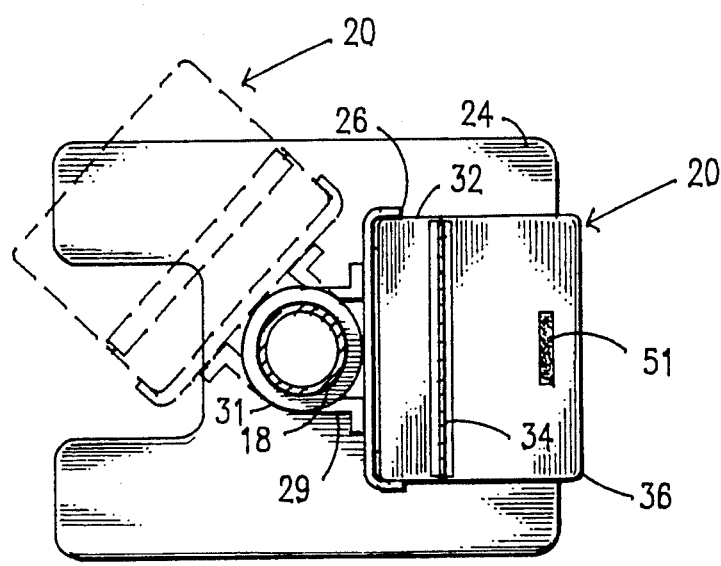
FIG. 5 is a top plan view of the containers of FIG. 4 mounted to a round post with a changed position in phantom.
Figure 6:
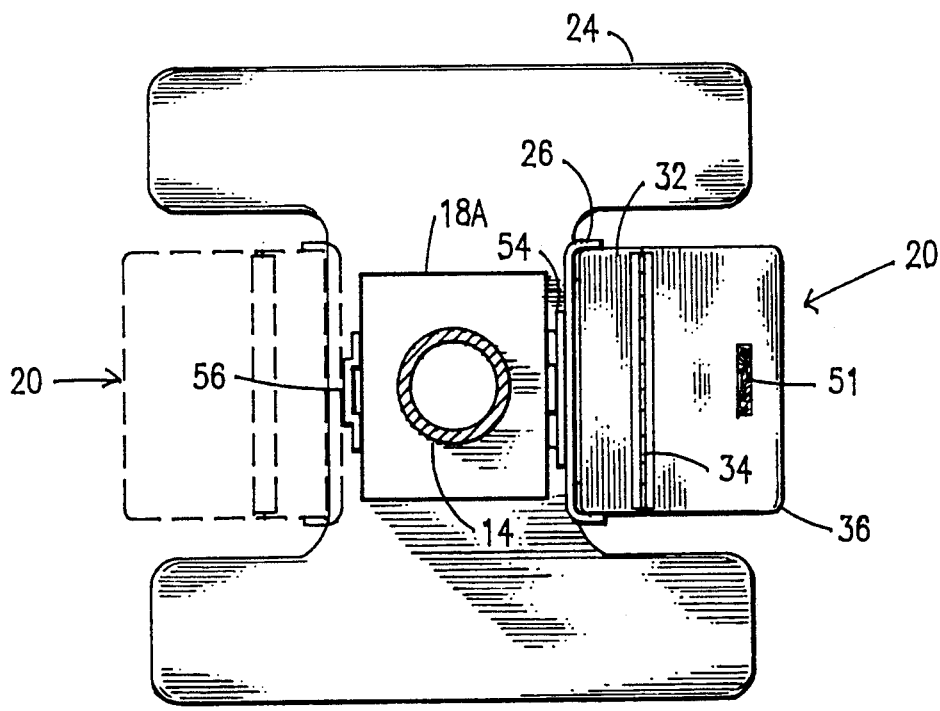
FIG. 6 is a top plan view of the container of FIG. 2 mounted to a squared post with a changed position in phantom.

As seen in FIGS. 1 and 7, when connecting the container 20 to a round post 18, rings 30 and 31 are clamped around post 18 by screwing its two hemispheres together using pre-drilled holes. These rings 30 and 31 prevent the containers 20 from moving upwards or downwards along post 18. However, U-clamp 28 and 29 are loosely engaged to post 18 so that the containers 20A, B and C can be swiveled around post 18 as seen in FIG. 5.

Figure 3:
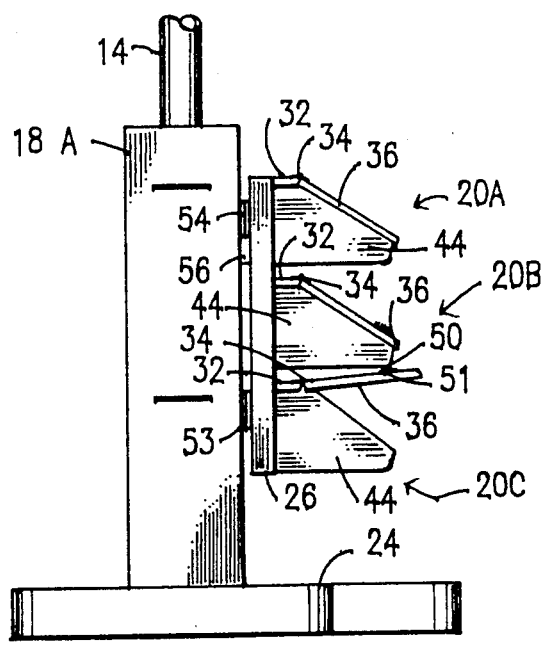
FIG. 3 is a partial side elevational view of three storage containers connected to a four sided microscope post.
Figure 4:
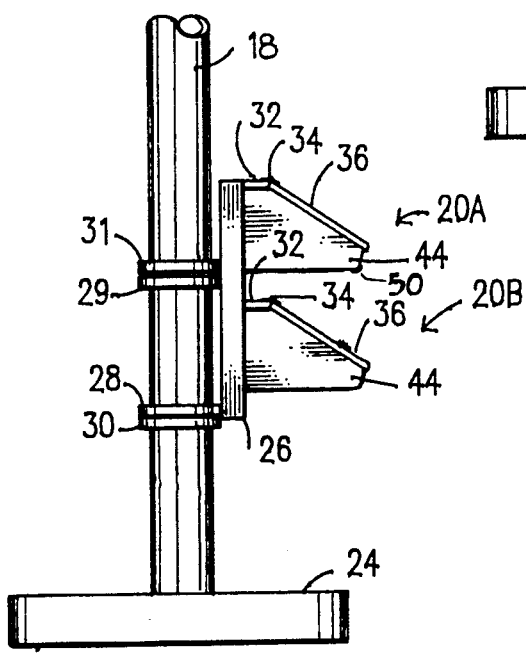
FIG. 4 is a partial side elevation view of two storage containers connected to a round post.

As seen in FIGS. 2, 3 and 8, a bracket 56 is screwed to post 18A to provide a slot 64 for insertion of T-bracket 54. The bottom tab 66 in T-bracket 54 fits into slot 64 to retain the container apparatus in place on a four sided post. T-bracket 54 is affixed to back plate 26 by screws 58, washers 68 and bolts 60. A spacer plate 53 affixed by similar bolts and nuts to back plate 26 keeps an equal space between the back of plate 26 and the post 18A.

A back plate 52 inserted between plate 26 and the back wall 46 of container 20 ensures a tight fit of the container 20 within the back plate 26.

A foam material 62 is inserted over the bottom 48 of container 20 to prevent breakage of the delicate microscope accessories placed within container 20.

The containers 20A, B or C are made from a flame resistant acrylic polyvinyl chloride alloy polymer. A typical material is KYDEX ® 100 which has passed U L laboratories' 94 flamability rating.

The containers shown in FIG. 1 attached to a round post 18 can turn in a 360° circle so that the microscope accessories found in the containers 20 can be easily repositioned to accommodate any operating room equipment set up.

The T-brackets 54 on the back of plate 26 permit easy movement of the containers 20 on two sides of the post 18A. A bracket 56 containing a slot 64 must be affixed to two sides of the post 18A. The plate 52, back plate 26 and various brackets are all made from similar flame resistant polymer as described for the containers 20. The ring bracket 30 is manufactured of a low friction bearing material such as a high molecular weight plastic.

Equivalent brackets and support members may be employed with the containers of this invention without departing from the scope of this invention.

Having thus described the invention, what is claimed and desired to be secured by Letters Patent is:

1. On a surgical stand having an upright post mounted on a supporting member resting on a floor and at least one microscope and supporting apparatus pivotably mounted on an upper portion of the post, the improvement comprising a microscope accessory equipment container mounted on a portion of the post below said at least one microscope, the container having a planar rectangular ceiling with a hinged lid along a front edge of the ceiling, the hinged lid descending downwardly from the front edge to rest on a top edge of a front wall, the front wall being joined on opposite side edges to front edges of a right and a left side wall, the side walls being joined at opposite bottom edges to a planar floor, at opposite top edges to the ceiling and on opposite rear side edges to an upright back wall, the back wall being joined to a rear edge of the ceiling, the hinged lid spanning a gap between the side walls and between the ceiling and the planar floor to form a closed container when the hinged lid is resting on the top edge of the front wall.

2. The improved surgical stand of claim 1 wherein the container is mounted on a round post by one or more U-clamps joined to an upright supporting plate, the plate joined to the back wall of the container.

3. The improved surgical stand of claim 2 wherein there is an upper and lower container joined to the supporting plate in a vertical configuration.

4. The improved surgical stand of claim 2 wherein there is an upper, middle and lower container joined to the supporting plate in a vertical configuration.

5. The improved surgical stand of claim 1 wherein the microscope accessory equipment container is mounted on a squared post by one or more brackets joined to an upright supporting plate, the plate joined to the back wall of the container.

6. The improved surgical stand of claim 5 wherein there are two containers joined to the supporting plate in a vertical configuration.

7. The improved surgical stand of claim 5 wherein there are three containers joined to the supporting plate in a vertical configuration.

8. The improved surgical stand of claim 1 wherein the microscope accessory equipment container is made from an acrylic-polyvinyl chloride alloy.

9. The improved surgical stand of claim 1 wherein the microscope accessory equipment container encloses microscope lenses.

10. The improved surgical stand of claim 1 wherein a top surface of the hinged lid contains a strip of hook or loop material which engages a corresponding hook or loop material mounted on the post above the container.

11. The improved surgical stand of claim 3 wherein the hinged lid of the lower container contains a strip of hook or loop material engageable with a corresponding hook or loop material on a lower front edge of the front wall on the upper container.

12. The improved surgical stand of claim 4 wherein the hinged lid of the lower container contains a strip of hook or loop material engageable with a corresponding hook or loop material on a lower front edge of the front wall on the middle container and the hinged lid of the middle container contains a strip of hook or loop material engageable with a corresponding hook or loop material on a lower front edge of the front wall on the upper container.

13. A surgical stand having an upright post mounted on a supporting member resting on a floor and at least one microscope and supporting apparatus pivotably mounted on an upper portion of the post, a lower portion of the post having at least one microscope accessory equipment container movably attached, the container comprising a planar rectangular ceiling with a hinged lid along a front edge of the ceiling, the hinged lid descending downwardly from the front edge to rest on a top edge of a front wall, the front wall being joined on opposite side edges to front edges of a right and a left side wall, the side walls being joined at opposite bottom edges to a planar floor, at opposite top edges to the ceiling and on opposite rear side edges to an upright back wall, the back wall being joined to a rear edge of the ceiling, the hinged lid spanning a gap between the side walls and between the ceiling and the planar floor to form a closed container when the hinged lid is resting on the top edge of the front wall.

14. The surgical stand of claim 13 wherein each container is mounted on a round post to move around 360° in a plane parallel to the supporting member, each container joined by its back wall and multiple bolts to an upright supporting plate, the upright supporting plate, joined to the round post by U-clamps.

15. The surgical stand of claim 14 wherein there is an upper and lower container joined to the supporting plate in a vertical configuration.

16. The surgical stand of claim 14 wherein there is an upper, middle and lower container joined to the supporting plate in a vertical configuration.

17. The surgical stand of claim 13 wherein the microscope accessory equipment container is mounted on a squared post by one or more brackets joined to an upright supporting plate, the plate joined to the back wall of the container.

18. The improved surgical stand of claim 17 wherein there are two containers joined to the supporting plate in a vertical configuration.

19. The surgical stand of claim 17 wherein there are three containers joined to the supporting plate in a vertical configuration.

20. The surgical stand of claim 13 wherein the hinged lid of a first container contains a strip of hook or loop material engageable with a corresponding hook or loop material on a lower front edge of the front wall on a second container located in a vertical position above the first container.

* * * * *